United States Patent
Hirotani et al.

[11] Patent Number: 6,100,303
[45] Date of Patent: Aug. 8, 2000

[54] METHOD OF PRODUCING METHANOL

[75] Inventors: Kunio Hirotani, Chiba; Hitoshi Nakamura, Yotsukaidou; Kazuo Shouji, Funabashi, all of Japan

[73] Assignee: Toyo Engineering Corporation, Tokyo, Japan

[21] Appl. No.: 09/341,693

[22] PCT Filed: Nov. 26, 1998

[86] PCT No.: PCT/JP98/05317

§ 371 Date: Jul. 26, 1999

§ 102(e) Date: Jul. 26, 1999

[87] PCT Pub. No.: WO99/28281

PCT Pub. Date: Jun. 10, 1999

[30] Foreign Application Priority Data

Nov. 27, 1997 [JP] Japan ................................. 9-363346
Nov. 24, 1998 [JP] Japan ............................... 10-332941

[51] Int. Cl.⁷ .................................................. C07C 27/00
[52] U.S. Cl. ........................... 518/703; 518/700; 518/713
[58] Field of Search .................... 518/703, 700, 518/713

[56] References Cited

U.S. PATENT DOCUMENTS 4,443,561  4/1984  Boelema et al. ..................... 518/704
5,512,599  4/1996  Hiramatsu et al. ................... 518/703

FOREIGN PATENT DOCUMENTS 4-364142   12/1992   Japan .
10-259148   9/1998   Japan .

*Primary Examiner*—Johann Richter
*Assistant Examiner*—J. Parsa
*Attorney, Agent, or Firm*—Oblon, Spivak, McClelland, Maier & Neustadt, P.C.

[57] ABSTRACT

The present invention provides a process for producing methanol which gives reduced construction costs of plant and improved energy efficiency of the whole plant. According to this process for producing methanol, methanol is manufactured by subjecting a feedstock mixed gas comprising a feedstock gas and steam to primary reforming, to secondary reforming, and then to methanol synthesis reaction. In this case, the primary reforming means is composed of fired-heating type steam reformer and heat-exchange type steam reformer, the feed rate of the feedstock mixed gas to the fired-heating type steam reformer and that to the heat-exchange type steam reformer are in a proportion of 1 to 3–3 to 1, part of the feedstock gas with sulfur removed, air for combustion, unreacted synthesis gas generated in the methanol synthesis loop and preferably a flash gas are supplied to the fired-heating type steam reformer as fuel, the synthesis gas from the secondary reforming reaction is fed to the heat-exchange type steam reformer to heat the feedstock mixed gas for the steam reformer, and steam generated by the heat of reaction in the methanol reactor is mixed with the feedstock gas supplied to the primary reforming means.

4 Claims, 1 Drawing Sheet

METHOD OF PRODUCING METHANOL

This application is a 371 of PCT/JP98/05317 filed on Nov. 26, 1998.

TECHNICAL FIELD

This invention relates to a process for producing methanol by subjecting a feedstock gas composed mainly of natural gas to primary reforming and secondary reforming to convert the feedstock gas to a synthesis gas comprising hydrogen, carbon monoxide and carbon dioxide and producing methanol from the synthesis gas.

BACKGROUND ART

Processes for producing methanol from hydrogen and carbon oxides are based on the following two reactions:

$$CO+2H_2=CH_3OH$$

$$CO_2+3H_2=CH_3OH+H_2O$$

Accordingly, in the synthesis of methanol, if the relation (R) among the mol percentages of CO, $CO_2$ and $H_2$ is 2.0 as calculated according to the following equation, the relation is regarded to be stoichiometric:

$$R=(H_2 \text{ mol }\%-CO_2 \text{ mol }\%)/(CO \text{ mol }\%+CO_2 \text{ mol }\%)$$

Consequently, it is common to think that a synthesis gas, which has a composition very close or equivalent to the aforesaid stoichiometric composition demanded for methanol synthesis, namely, a composition that makes R=2.0, should be produced.

As a conventional process, Japanese Patent Publication No. 46961/1980 discloses a process which comprises dividing a feedstock gas into two streams, subjecting one of the streams to conventional steam reforming to form an effluent gas, combining the effluent gas with the other stream, and subjecting the combined stream to secondary reforming using oxygen, thereby producing a synthesis gas having the stoichiometric composition (R=2.0) suitable for methanol synthesis. Further, the Japanese Patent Laid-Open Publication No. 3614/1990 proposes to use the enthalpy of a product from the secondary reforming using oxygen, as a heat source for the primary reforming by steam.

However, when R is made 2.0 as in the above prior art processes, loss of energy is increased due to increase in the consumption of oxygen, though the energy for compressing the synthesis gas is reduced.

Further, as a process to solve the problems of the above prior art processes, Japanese Patent Laid-Open Publication No. 4140/1985 teaches a process for producing a methanol synthesis gas from natural gas as a feedstock through primary steam reforming and secondary oxygen combustion reforming, wherein the primary reforming conditions, secondary reforming conditions and amount of oxygen supply are so created that the synthesis gas may have a composition of R=2.2–2.5 and in consequence the energy efficiency of the whole plant including oxygen production, synthesis gas production and methanol synthesis becomes higher than that of the case of R=2.0.

However, this process involves a problem of limits in fabricating the combustion-type steam reforming furnace used in the primary steam reforming and a problem of reliability for the uniform distribution of the feedstock into a large number, such as more than a thousand, of reaction tubes.

Further, the aforesaid process of Japanese Patent Laid-Open Publication No. 3614/1990 has no combustion system for effectively burning purge gas from the synthesis loop as a fuel within the process system. Therefore, it needs new installation of a gas turbine and requires large plant investments to maintain the efficiency of the system. In addition, the process cannot maintain its efficiency unless it sells excess heat to the outside by way of means such as exportation of power as occasion demands.

Plants for producing methanol from natural gas have recently been demanded to reduce costs with economical efficiency added and to further improve the energy efficiency of the whole methanol synthesis plant, in the construction of methanol plants that are significantly increasing in size due to the production of fuel methanol.

DISCLOSURE OF THE INVENTION

It is an object of the present invention to provide a process for producing methanol which improves the energy efficiency of a whole plant for the synthesis of methanol including the production of methanol synthesis gas.

As a result of intensive investigation to solve the aforesaid problems of the prior art, the inventors have found that the energy efficiency of the whole plant is significantly improved by the process described below.

The process for producing methanol according to the present invention is a process which comprises subjecting a feedstock gas comprising hydrocarbons having atomic ratios H/C of hydrogen (H) to carbon (C) of 3–4 or a feedstock gas formed by treating hydrocarbons having atomic ratios H/C of 2–3 in a prereformer to primary reforming under the conditions of a pressure of 15–40 Kg/cm²-G, a catalyst outlet temperature of 700–850° C. and a molar ratio S/C of steam (S) to carbon in the feedstock gas of 2.5–4.0 and then to secondary reforming using oxygen having a purity of 95% or more under the conditions of a pressure of 15–40 Kg/cm²-G and a catalyst outlet temperature of 950–1,000° C. to obtain a synthesis gas in which the relation (R) among the mol percentages of hydrogen, carbon monoxide and carbon dioxide is 2.2–2.5 as calculated according to the following equation $$R=(H_2 \text{ mol }\%-CO_2 \text{ mol }\%)/(CO \text{ mol }\%+CO_2 \text{ mol }\%)$$

and subjecting said synthesis gas to methanol synthesis at a pressure of 40–100 Kg/cm²-G and a catalyst temperature of 210–300° C. to produce methanol, wherein said primary reforming comprises fired-heating type (conventional) steam reforming and heat-exchange type steam reforming, said feedstock gas with sulfur removed is mixed with steam to obtain a feedstock mixed gas having an S/C of 2.5–4.0, the feedstock mixed gas is fed to said fired-heating type steam reforming and said heat-exchange type steam reforming in a proportion of 1 to 3–3 to 1, said fired-heating type steam reforming is effected by using as the heat source a combustion gas formed by burning part of said feedstock gas with sulfur removed and a synthesis purge gas generated to remove inert components accumulated in the methanol synthesis loop, the combustion gas discharged from said fired-heating type steam reforming is heat-exchanged with said feedstock mixed gas introduced into said fired-heating type steam reforming to heat said feedstock mixed gas, while said heat-exchange type steam reforming is effected by causing said feedstock mixed gas to exchange heat with said synthesis gas from said secondary reforming to heat said feedstock mixed gas, and steam generate by the recovery of reaction heat in said methanol synthesis is used as steam for mixing with said feedstock gas fed to said primary reforming.

BEST MODE FOR CARRYING OUT THE INVENTION

Figure 1:
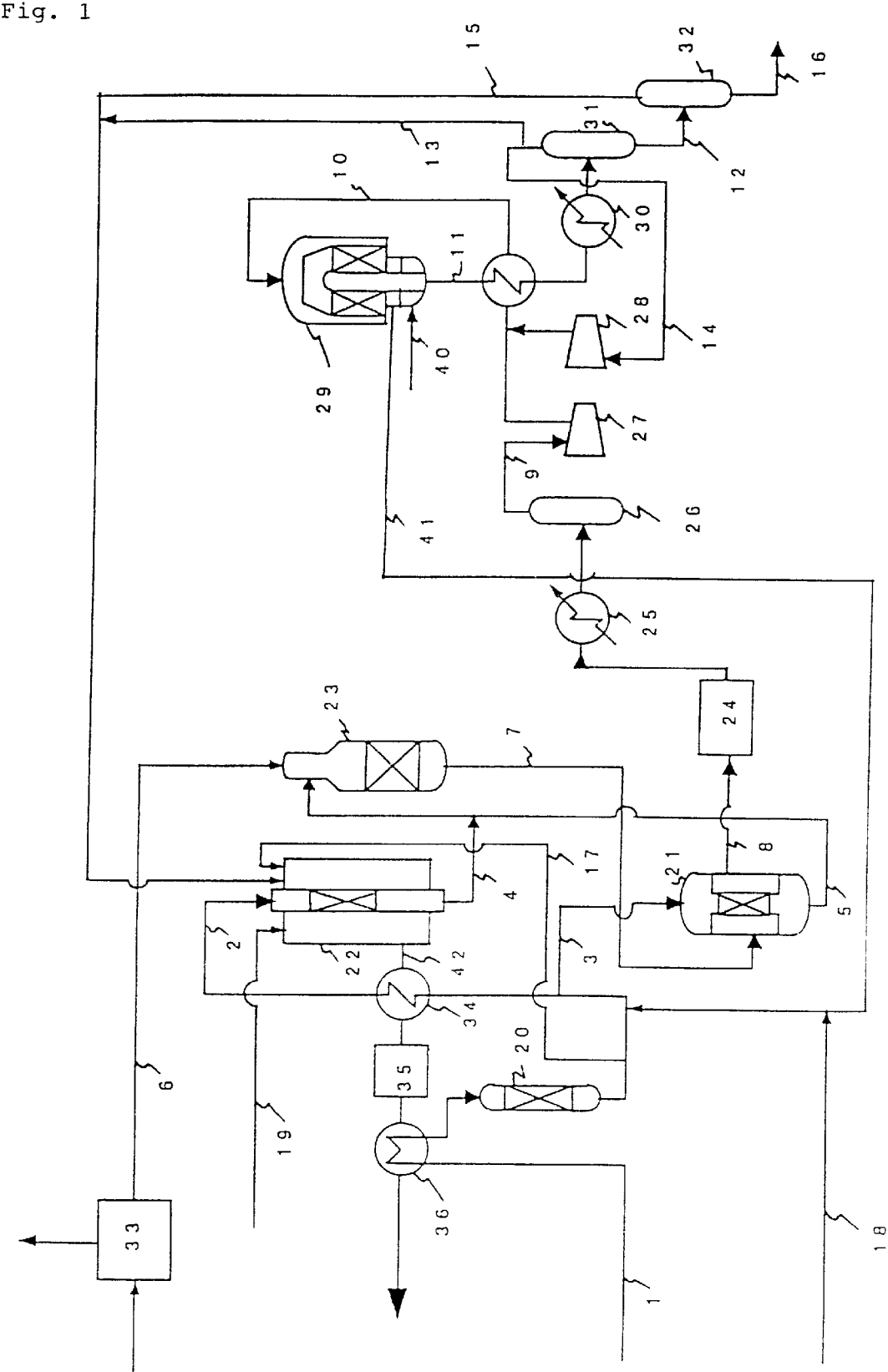
FIG. 1 is a flowsheet of a process for producing methanol according to the present invention.

The feedstock gas used in the present invention is a hydrocarbon gas having an atomic ratio of 3–4, for example, natural gas composed mainly of methane, or a hydrocarbon gas having an atomic ratio H/C of 3–4 obtained, as is well known, by preliminarily reforming a liquid hydrocarbon having an atomic ratio H/C of 2–3, such as naphtha, with steam in a prereformer at a temperature of 250–550° C. in the presence of a catalyst composed primarily of nickel oxide by way of example.

In the present invention, the primary reforming means comprises a fired-heating type steam reformer and a heat-exchange type steam reformer, and a feedstock mixed gas formed by mixing steam with the feedstock gas with sulfur removed is fed to both of the fired-heating type steam reformer and the heat-exchange type steam reformer. By controlling the rates of feed in a proportion of 1 to 3–3 to 1, it becomes possible for the fired-heating type steam reformer to use a part of unreacted synthesis gas generated in the methanol synthesis loop and a flash gas as the greater part of the fuel. Separately, in the heat-exchange type steam reformer, it has become possible to utilize a synthesis gas having completed the secondary reforming reaction to exchange heat with the feedstock mixed gas.

In the present invention, steam generated by the heat of reaction in the methanol synthesis reactor is mixed with the feedstock gas supplied to the primary reforming means. As a result, the amount of steam supplied from the outside can be minimized and the energy generated inside the plant can be effectively utilized.

Further, the enthalpy of the product from the secondary reforming is used as a heat source to furnish ¼–¾ of the heat quantity required for the primary steam reforming, and the amount of oxygen supply is so set that the synthesis gas may have a composition of R=2.2–2.5 to regulate the purge gas from the synthesis to be substantially balanced with the amount of fuel necessary for the combustion type steam reforming furnace of the primary reforming. Consequently, the fuel required for the primary reforming is saved and the compression power for oxygen can be reduced, improving the energy efficiency of the whole plant by 1–2%.

Where the enthalpy of the product from the secondary reforming is used as a heat source to furnish ¼ or less of the heat quantity required for the primary reforming, it cannot be expected to save 10% or more of the fuel required for the primary reforming, while on the contrary where ¾ or more of the heat quantity is furnished by the enthalpy, it becomes impossible to produce a synthesis gas of R=2.2–2.5.

The heat required for the heat-exchange type steam reforming in the primary reforming is obtained by partial oxidation reaction in the secondary reforming. The amount of oxygen necessary to carry out the partial oxidation gives effects also on the composition of the synthesis gas having completed the secondary reforming reaction.

Therefore, where the amount of oxygen supply is so set that the synthesis gas may have a composition of R=2.2–2.5, the load of the heat-exchange type steam reformer being determined, and the distribution of the feedstock mixed gas is determined, the relation (R) and the load distribution between the fired-heating type steam reformer and the heat-exchange type steam reformer are so regulated that the purge gas from the methanol synthesis may substantially be balanced with the amount of fuel necessary for the fired-heating type steam reformer in the primary reforming.

Then, the present invention is illustrated in detail with reference to FIG. 1. A feedstock gas composed primarily of methane, such as natural gas, is supplied through a line 1, raised in temperature to a desulfurization temperature of about 400° C. by a feedstock preheater 36, in which the waste heat of a combustion gas from a combustion type steam reforming furnace 22 is utilized, and fed to a desulfurizer 20 to remove completely sulfur, that is a catalyst poison of steam reforming catalysts. The feedstock gas with surfur removed is mixed with steam fed through a line 18. At the same time, steam generated in a methanol synthesis reactor 29 is recovered and mixed with the feedstock gas by way of a line 41. In consequence, it is sufficient if the steam fed through the line 18 from the outside makes up only the deficit between the amount of steam necessary in the primary reforming means and that of the steam through the line 41. This may save about 70% of the amount of steam required in the prior art processes.

The feedstock gas is supplied partially to the combustion type steam reforming furnace 22 by way of a line 17 as a desulfurized auxiliary fuel for the combustion type steam reforming furnace 22, prior to being mixed with steam.

A feedstock mixed gas, in which the feedstock gas is mixed with steam, is supplied to a heat-exchange type steam reformer 21 through a line 3 and the fired-heating type steam reformer 22 via a line 2 after being heated to about 560° C. in a mixed gas heater 34. The proportion of the feed rate of the feedstock mixed gas sent to the heat-exchange type reformer 21 to that of the gas sent to the fired-heating type reformer 22 may be 1 to 3–3 to 1.

Although not shown in the drawing, the feedstock mixed gas in the line 3 to be sent to the heat-exchange type steam reformer 21 may first be heated in the mixed gas heater 34, if the burned gas supplied through a line 42 contains enough heat, and then be branched to the heat-exchange type steam reformer 21 from the feed line 2 to the fired-heating type steam reformer 22. Further, the feedstock mixed gas may be supplied to the heat-exchange type reformer 21 after being heated in a mixed gas heater installed separately on the line 3. Alternatively, the mixed gas may be supplied to the heat-exchange type steam reformer 21 after being heat-exchanged with a reformed gas from the same reformer 21.

As the fuel for the fired-heating type steam reformer 22, a purge gas from the methanol synthesis loop, a flash gas and auxiliary fuel are fed to the fired-heating type reformer 22 via a line 13, line 15 and line 17, respectively, and air for combustion is supplied through a line 19 so that the fuel is burned by means of low NOx burners, producing the reaction heat for the steam reforming. The fired-heating type steam reformer 22 is constructed by installing in parallel a plurality of reaction tubes packed with a nickel-base catalyst. The operating conditions at the outlet of the reaction tubes are in the range of 15–40 $Kg/cm^2$-G in pressure and 700–850° C. in temperature. An example of the conditions is such that the pressure is 19.4 $Kg/cm^2$-G, the temperature is 800° C., and the residual amount of unreformed methane is 10.6 dry mol %.

The temperature of the burned gas which has imparted the reaction heat to the tubular reactor is about 1,000° C., and the gas is sent to the mixed gas heater 34, a heat recovery unit 35 for preheating boiler water and a feedstock preheater 36 via the line 42 from the combustion type steam reforming furnace 22 to further recover the waste heat.

Separately, the feedstock mixed gas sent to the heat-exchange type steam reformer 21 through the line 3 is given the reaction heat by exchanging heat with a synthesis gas having a temperature of 950–1,000° C. discharged from a secondary reformer 23 to a line 7. The feedstock mixed gas for the heat-exchange type steam reformer 21 is passed inside the tubes where a nickel-base catalyst is packed. The operating conditions at the outlet of the tubes are such that the pressure is 19.4 Kg/cm$^2$-G, the temperature is 820° C., and the residual amount of unreacted methane is 9.5 dry mol %, for instance.

Synthesis gases each containing about 5–15% of unreformed methane from the respective steam reforming reactions are sent to the secondary reformer 23 via lines 4 and 5 to reform the unreformed methane. Oxygen of 95–99% concentration is fed to the secondary reformer 23 through a line 6 by way of an air separator 33. The amount of oxygen supply is so regulated that the relation (R) among the mol percentages of hydrogen, carbon monoxide and carbon dioxide, that are a composition of the synthesis gas at the outlet of the secondary reformer, may become 2.2–2.5 as calculated according to the following equation:

$$R = (H_2 \text{ mol \%} - CO_2 \text{ mol \%})/(CO \text{ mol \%} + CO_2 \text{ mol \%})$$

The operating conditions at the outlet of the secondary reformer 23 are in the range of 15–40 Kg/cm$^2$-G in pressure and 950–1,000° C. in temperature, and an example of the conditions is such that the pressure is 19.0 Kg/cm$^2$-G, the temperature is 950–1,000° C., and the residual amount of unreformed methane is 0.4 dry mol %. The synthesis gas, passed through the shell-side of the heat-exchange type reformer 21 via the line 7 to furnish the reaction heat of the steam reforming, is sent through a line 8 to a heat recovery unit 24 for preheating boiler water, to a cooler 25 to condense water, and then to a condensed water separator 26 to separate the condensed water.

The synthesis gas is sent through a line 9 to a synthesis gas compressor 27 where it is pressurized to 40–100 Kg/cm$^2$-G, for example, to 100 Kg/cm$^2$-G. The pressurized synthesis gas is fed to a methanol synthesis reactor 29 by way of a line 10. However, before being fed to the methanol synthesis reactor 29, the pressurized synthesis gas is mixed with unreacted synthesis gas discharged from a methanol separator 31 to a line 14, and is then heat-exchanged with a synthesis gas taken out from the methanol synthesis reactor 29 to a line 11, so that the mixed synthesis gas is raised in temperature to 210–240° C.

The methanol synthesis reaction is carried out under the conditions of, for example, a pressure of 40–100 Kg/cm$^2$-G and a temperature of 210–300° C. as is well known in the art. Here, boiler water is fed to the methanol synthesis reactor 29 through a line 40, and the heat of reaction is recovered as steam via a line 41. The steam is used as steam for steam reforming.

An unreacted synthesis gas containing about 7% of product methanol from the methanol synthesis reactor 29 is taken out through the line 11, heat-exchanged with the synthesis gas fed to the methanol synthesis reactor 29, passed to a condenser 30 to condense the product methanol and then sent to a methanol separator 31 to separate the condensed crude methanol from the unreacted synthesis gas. The most part of the unreacted synthesis gas is circulated to the methanol synthesis reactor 29 by means of a circulating compressor 28, while the rest is sent to the combustion type steam reforming furnace 22 via a line 13 as a purge gas to remove accumulated inert components so that it is effectively utilized in the furnace 22 as fuel. If inert methane and nitrogen are accumulated in large amounts within the synthesis loop, the partial pressures of hydrogen, carbon monoxide and carbon dioxide in the methanol synthesis reactor 29 are reduced so that adequate amounts of the inert components have to be purged from the circulation loop to prevent the efficiency of the methanol synthesis from degrading.

Since the crude methanol of a line 12 separated in the methanol separator 31 contains gaseous components dissolved under high pressure, it is flashed by reducing pressure in a let-down drum 32 to discharge the dissolved gaseous components to a line 15, the flash gas being also used as a fuel for the combustion type reforming furnace 22.

Separately, the crude methanol with the dissolved gas removed is sent to a methanol refining unit through a line 16.

The present invention is illustrated in detail by referring to the following Examples and Comparative Examples in each of which a methanol plant of 10,000 tons per day production is designed.

EXAMPLE 1

Natural gas of the following composition is used as a feedstock. A combustion type steam reforming furnace and a heat-exchange type steam reformer are used as primary reforming units. Oxygen from an air separator is employed in secondary reforming. Process design parameters are regulated so that the relation (R) among the mol percentages of $CO_2$, $CO$ and $H_2$ in the synthesis gas may become 2.5, and production of the synthesis gas and synthesis of methanol are carried out under the conditions described below.

The material balance is shown in Table 1. The vertical column represents the number of each line given in FIG. 1, while the horizontal column shows the pressure, temperature, flow rate, and composition of substances flowing through each line.

TABLE 1

| Line number | Pressure Kg/cm$^2$-G | Temp. ° C. | Composition (mol %) | | | | | | | | | | Flow rate kmol/hr |
|---|---|---|---|---|---|---|---|---|---|---|---|---|---|---|
| | | | $CH_4$ | $H_2$ | CO | $CO_2$ | $O_2$ | $N_2$ | $H_2O$ | $CH_3OH$ | $C_2H_6$ | $C_3H_8$ | Others | |
| 1 | 27.0 | 40 | 98.50 | | | | | | | | 1.00 | 0.50 | | 13,492.5 |
| 2 | 25.0 | 560 | 27.75 | | | | | | 71.83 | | 0.28 | 0.14 | | 26,045.9 |
| 3 | 25.0 | 340 | 27.75 | | | | | | 71.83 | | 0.28 | 0.14 | | 21,852.5 |
| 4 | 19.4 | 800 | 7.15 | 46.49 | 7.93 | 5.77 | | | 32.66 | | | | | 35,883.5 |
| 5 | 19.4 | 819 | 6.49 | 47.42 | 8.67 | 5.45 | | | 31.96 | | | | | 30,455.8 |

TABLE 1-continued

| Line number | Pressure Kg/cm²-G | Temp. °C. | Composition (mol %) | | | | | | | | | | Flow rate kmol/hr |
|---|---|---|---|---|---|---|---|---|---|---|---|---|---|
| | | | CH₄ | H₂ | CO | CO₂ | O₂ | N₂ | H₂O | CH₃OH | C₂H₆ | C₃H₈ | Others | |
| 6 | 20.0 | 150 | | | | | 99.00 | 1.00 | | | | | | 3,265.2 |
| 7 | 19.0 | 975 | 0.39 | 49.90 | 13.06 | 4.93 | | 0.04 | 31.67 | | | | | 74,869.2 |
| 9 | 17.0 | 40 | 0.57 | 72.73 | 19.04 | 7.18 | | 0.06 | 0.42 | | | | | 51,369.5 |
| 10 | 100.0 | 240 | 2.59 | 88.31 | 5.40 | 3.00 | | 0.31 | 0.07 | 0.30 | | | 0.02 | 228,229.1 |
| 11 | 98.0 | 260 | 2.93 | 85.01 | 1.32 | 1.69 | | 0.35 | 1.79 | 6.80 | | | 0.02 | 202,112.1 |
| 12 | 96.0 | 40 | 0.18 | 0.41 | 0.04 | 0.61 | | 0.01 | 21.19 | 77.47 | | | 0.10 | 16,797.2 |
| 13 | 96.0 | 40 | 3.18 | 92.77 | 1.44 | 1.79 | | 0.38 | 0.04 | 0.39 | | | 0.02 | 8,265.0 |
| 14 | 96.0 | 40 | 3.18 | 92.77 | 1.44 | 1.79 | | 0.38 | 0.04 | 0.39 | | | 0.02 | 177,049.9 |
| 15 | 3.5 | 40 | 15.73 | 46.84 | 3.76 | 22.28 | | 0.74 | 0.57 | 6.36 | | | 3.71 | 143.1 |
| 16 | 3.5 | 40 | 0.05 | 0.01 | 0.01 | 0.42 | | 0.00 | 21.36 | 78.08 | | | 0.07 | 16,654.1 |
| 17 | 3.5 | 400 | 98.50 | | | | | | | | 1.00 | 0.50 | | 479.5 |
| 41 | 29.0 | 233 | | | | | | | 100.00 | | | | | 25,452.2 |

The energy efficiency of the whole plant was as shown in Table 6, and the overall unit energy consumption [G(giga) cal/ton-methanol] was 6.692.

| CH₄ | 98.50 mol % |
|---|---|
| C₂H₆ | 1.00 mol % |
| C₃H₈ | 0.50 mol % |

Distribution rate to primary reforming

| Combustion type steam reforming furnace | 54.4% |
|---|---|
| Heat-exchange type steam reformer | 45.6% |

Catalyst composition in combustion type steam reforming furnace

| Ni | 20 ± 2 wt % |
|---|---|
| Al₂O₃ | 72 to 75 wt % |
| CaO | <0.10 wt % |
| TiO₂ | <0.05 wt % |
| SiO₂ | <0.01 wt % |

Oxygen supply to secondary reformer

| Flow rate | 73,186 Nm³/hour |
|---|---|
| Purity | 99.0% |

Secondary reformer $R = (H_2 - CO_2)/(CO + CO_2) = 2.50$

Composition of catalyst used
Upper heat-resistant catalyst

| Cr₂O₃ | 6 ± 2 wt % |
|---|---|
| Al₂O₃ | 95 to 97 wt % |
| CaO | <0.10 wt % |
| TiO₂ | <0.05 wt % |
| SiO₂ | <0.10 wt % |

Lower reforming catalyst

| Ni | 16 ± 1 wt % |
|---|---|
| Al₂O₃ | 95 to 97 wt % |
| CaO | 0.10 wt % |
| Ti | 3.00 wt % |
| SiO₂ | 0.20 wt % |

Methanol reactor

Composition of catalyst used

| CuO | 20 to 50 wt % |
|---|---|
| ZnO | 15 to 60 wt % |
| Al₂O₃ | 5 to 30 wt % |
| MgO | 0.2 to 7 wt % |

| Temperature of catalyst bed | 240 to 260° C. |
|---|---|

EXAMPLE 2

Operation was carried out in the same manner as in Example 1, except that natural gas of the following composition was used as a feedstock. The material balance is shown in Table 2.

The energy efficiency of the whole plant was as shown in Table 6, and the overall unit energy consumption (Gcal/ton-methanol) was 6.714. The unit energy consumption was improved by 1.40% as compared with Comparative Example 2 of a conventional process. Further, the amount of fuel required for the fired-heating type reformer and the net consumption of fuel natural gas were reduced in comparison with Comparative Example 2.

Natural gas composition

| | |
|---|---|
| $CH_4$ | 95.60 mol % |
| $C_2H_6$ | 3.39 mol % |
| $C_3H_8$ | 0.09 mol % |
| $C_4H_{10}$ | 0.03 mol % |
| $C_5H_{12}$ | 0.01 mol % |
| $C_6H_{14}$ | 0.14 mol % |
| $N_2$ | 0.26 mol % |
| $CO_2$ | 0.47 mol % |
| $H_2O$ | 0.01 mol % |

Distribution rate to primary reforming means

| | |
|---|---|
| Fired-heating type steam reformer | 58.7% |
| Heat-exchange type steam reformer | 41.3% | as used in Example 2 was employed as a feedstock and process design parameters were so regulated that the relation (R) among the mol percentages of $CO_2$, CO and $H_2$ in the synthesis gas may become 2.25. The material balance is shown in Table 3.

Distribution rate to primary reforming means

| | |
|---|---|
| Fired-heating type steam reformer | 30.6% |
| Heat-exchange type steam reformer | 69.4% |

The energy efficiency of the whole plant was as shown in Table 6, and the overall unit energy consumption (Gcal/ton-methanol) was 6.711. The unit energy consumption was improved by 1.45% as compared with Comparative Example 2 of a conventional process. Further, the amount of

TABLE 2

| Line number | Pressure Kg/cm²-G | Temp. °C. | Composition (mol %) | | | | | | | | | | Flow rate kmol/hr |
|---|---|---|---|---|---|---|---|---|---|---|---|---|---|
| | | | $CH_4$ | $H_2$ | CO | $CO_2$ | $O_2$ | $N_2$ | $H_2O$ | $CH_3OH$ | $C_2H_6$ | $C_3H_8$ | Others | |
| 1 | 27.0 | 40 | 95.60 | | | 0.47 | | 0.26 | 0.01 | | 3.39 | 0.09 | 0.18 | 13,236.3 |
| 2 | 25.0 | 560 | 26.62 | | | 0.13 | | 0.07 | 72.16 | | 0.94 | 0.03 | 0.05 | 27,904.2 |
| 3 | 25.0 | 360 | 26.62 | | | 0.13 | | 0.07 | 72.16 | | 0.94 | 0.03 | 0.05 | 19,632.8 |
| 4 | 19.4 | 800 | 7.17 | 46.04 | 8.09 | 5.76 | | 0.05 | 32.89 | | | | | 38,494.7 |
| 5 | 19.4 | 846 | 4.95 | 49.73 | 5.19 | 4.95 | | 0.05 | 30.02 | | | | | 28,178.4 |
| 6 | 20.0 | 150 | | | | | 99.00 | 1.00 | | | | | | 2,984.4 |
| 7 | 19.0 | 975 | 0.41 | 50.18 | 13.23 | 4.89 | | 0.09 | 31.32 | | | | | 74,399.3 |
| 9 | 17.0 | 40 | 0.59 | 72.64 | 19.15 | 7.08 | | 0.13 | 0.41 | | | | | 51,389.8 |
| 10 | 100.0 | 240 | 2.67 | 87.87 | 5.41 | 3.00 | | 0.60 | 0.12 | 0.30 | | | 0.02 | 229,493.1 |
| 11 | 98.0 | 260 | 3.02 | 84.65 | 1.33 | 1.81 | | 0.68 | 1.81 | 6.76 | | | 0.02 | 203,305.1 |
| 12 | 96.0 | 40 | 0.19 | 0.40 | 0.04 | 0.62 | | 0.06 | 21.45 | 77.18 | | | 0.10 | 16,859.9 |
| 13 | 96.0 | 40 | 3.27 | 92.26 | 1.45 | 1.83 | | 0.39 | 0.74 | 0.39 | | | 0.02 | 8,342.0 |
| 14 | 96.0 | 40 | 3.27 | 92.26 | 1.45 | 1.83 | | 0.39 | 0.74 | 0.39 | | | 0.02 | 168,859.9 |
| 15 | 3.5 | 40 | 23.26 | 45.68 | 3.72 | 22.63 | | 1.42 | 0.83 | 6.34 | | | 3.66 | 145.7 |
| 16 | 3.5 | 40 | 0.05 | 0.01 | 0.00 | 0.43 | | 0.00 | 21.64 | 77.80 | | | 0.07 | 16,714.2 |
| 17 | 3.5 | 400 | 95.60 | | | 0.47 | | 0.26 | 0.01 | | 3.39 | 0.09 | 0.18 | 684.0 |
| 41 | 29.0 | 233 | | | | | | | 100.00 | | | | | 25,081.8 |

EXAMPLE 3

Operation was carried out under the same conditions as in Example 1 except that natural gas of the same composition fuel required for the fired-heating type reformer and the net consumption of fuel natural gas were reduced in comparison with Comparative Example 2.

TABLE 3

| Line number | Pressure Kg/cm²-G | Temp. °C. | Composition (mol %) | | | | | | | | | | Flow rate kmol/hr |
|---|---|---|---|---|---|---|---|---|---|---|---|---|---|
| | | | $CH_4$ | $H_2$ | CO | $CO_2$ | $O_2$ | $N_2$ | $H_2O$ | $CH_3OH$ | $C_2H_6$ | $C_3H_8$ | Others | |
| 1 | 27.0 | 40 | 95.60 | | | 0.47 | | 0.26 | 0.01 | | 3.39 | 0.09 | 0.18 | 12,975.1 |
| 2 | 25.0 | 560 | 26.62 | | | 0.13 | | 0.07 | 72.16 | | 0.94 | 0.03 | 0.05 | 14,259.2 |
| 3 | 25.0 | 360 | 26.62 | | | 0.13 | | 0.07 | 72.16 | | 0.94 | 0.03 | 0.05 | 32,339.4 |
| 4 | 19.4 | 800 | 7.17 | 46.04 | 8.09 | 5.76 | | 0.05 | 32.89 | | | | | 19,671.0 |
| 5 | 19.4 | 726 | 12.45 | 36.41 | 4.25 | 6.26 | | 0.06 | 40.57 | | | | | 40,840.5 |
| 6 | 20.0 | 150 | | | | | 99.00 | 1.00 | | | | | | 4,629.1 |
| 7 | 19.0 | 975 | 0.28 | 46.54 | 12.59 | 5.60 | | 0.11 | 34.87 | | | | | 73,137.9 |
| 9 | 17.0 | 40 | 0.43 | 71.17 | 19.26 | 8.57 | | 0.17 | 0.41 | | | | | 47,827.5 |
| 10 | 100.0 | 240 | 3.24 | 87.20 | 4.68 | 3.00 | | 0.31 | 0.11 | 0.31 | | | 0.02 | 254,243.3 |
| 11 | 98.0 | 260 | 3.61 | 84.01 | 1.21 | 1.62 | | 1.61 | 1.21 | 6.06 | | | 0.02 | 228,095.6 |
| 12 | 96.0 | 40 | 0.21 | 0.37 | 0.03 | 0.57 | | 0.03 | 23.85 | 74.84 | | | 0.09 | 17,388.1 |
| 13 | 96.0 | 40 | 3.89 | 90.91 | 1.31 | 1.71 | | 1.74 | 1.31 | 0.39 | | | 0.02 | 4,291.7 |
| 14 | 96.0 | 40 | 3.89 | 90.91 | 1.31 | 1.71 | | 1.74 | 1.31 | 0.39 | | | 0.02 | 206,415.8 |
| 15 | 3.5 | 40 | 18.60 | 43.34 | 3.30 | 21.14 | | 0.63 | 3.30 | 6.18 | | | 3.53 | 146.8 |
| 16 | 3.5 | 40 | 0.05 | 0.01 | 0.00 | 0.39 | | 0.00 | 24.05 | 75.43 | | | 0.06 | 17,241.3 |

TABLE 3-continued

| Line number | Pressure Kg/cm$^2$-G | Temp. °C. | Composition (mol %) | | | | | | | | | | Flow rate kmol/hr |
|---|---|---|---|---|---|---|---|---|---|---|---|---|---|
| | | | CH$_4$ | H$_2$ | CO | CO$_2$ | O$_2$ | N$_2$ | H$_2$O | CH$_3$OH | C$_2$H$_6$ | C$_3$H$_8$ | Others | |
| 17 | 3.5 | 400 | 95.60 | | | 0.47 | 0.26 | | 0.01 | | 3.39 | 0.09 | 0.18 | 301.7 |
| 41 | 29.0 | 233 | | | | | | | 100.00 | | | | | 24,082.4 |

COMPARATIVE EXAMPLE 1

Operation was carried out under the same conditions as in Example 1, except that natural gas of the same composition as used in Example 2 was employed as a feedstock and process design parameters were so regulated that the relation (R) among the mol percentages of CO$_2$, CO and H$_2$ in the synthesis gas may become 2.0. The material balance is shown in Table 4.

Distribution rate to primary reforming means

| | |
|---|---|
| Fired-heating type steam reformer | 4.1% |
| Heat-exchange type steam reformer | 95.9% |

The energy efficiency of the whole plant was as shown in Table 6, and the overall unit energy consumption (Gcal/ton-methanol) was 6.848. The unit energy consumption was degraded by 0.57% as compared with Comparative Example 2 of a conventional process. The amount of oxygen required and the total power requirements were increased in comparison with Example 1, Example 2 and Comparative Example 2.

COMPARATIVE EXAMPLE 2

Operation was carried out under the same conditions as in Example 1 except that the primary reforming means was carried out in the conventional manner using only a fired-heating type steam reformer, natural gas of the same composition as used in Example 2 being employed as a feedstock, and process design parameters were so regulated that the relation (R) among the mol percentages of CO$_2$, CO and H$_2$ in the synthesis gas may become 2.5. The material balance is shown in Table 5.

TABLE 4

| Line number | Pressure Kg/cm$^2$-G | Temp. °C. | Composition (mol %) | | | | | | | | | | | Flow rate kmol/hr |
|---|---|---|---|---|---|---|---|---|---|---|---|---|---|---|
| | | | CH$_4$ | H$_2$ | CO | CO$_2$ | O$_2$ | N$_2$ | H$_2$O | CH$_3$OH | C$_2$H$_6$ | C$_3$H$_8$ | Others | |
| 1 | 27.0 | 40 | 95.60 | | | 0.47 | 0.26 | 0.21 | | | 3.39 | 0.09 | 0.18 | 12,795.2 |
| 2 | 25.0 | 560 | 26.26 | | | 0.13 | | 0.07 | 72.16 | | 0.94 | 0.03 | 0.05 | 1,874.9 |
| 3 | 25.0 | 368 | 26.26 | | | 0.13 | | 0.07 | 72.16 | | 0.94 | 0.03 | 0.05 | 44,077.6 |
| 4 | 19.4 | 800 | 7.17 | 46.04 | 8.09 | 5.76 | | 0.05 | 32.89 | | | | | 2,586.4 |
| 5 | 19.4 | 660 | 16.59 | 28.11 | 1.98 | 5.92 | | | 47.34 | | | | | 522,201.6 |
| 6 | 20.0 | 150 | | | | | 99.00 | 1.00 | | | | | | 6,255.4 |
| 7 | 19.0 | 975 | 0.19 | 42.86 | 11.89 | 6.36 | | 0.13 | 38.53 | | | | | 72,273.9 |
| 9 | 17.0 | 40 | 0.30 | 69.49 | 19.28 | 10.31 | | 0.21 | 0.41 | | | | | 44,575.9 |
| 10 | 100.0 | 240 | 8.21 | 72.69 | 3.79 | 3.00 | | 11.34 | 0.10 | 0.38 | | | 0.02 | 340,623.2 |
| 11 | 98.0 | 260 | 9.43 | 69.00 | 1.35 | 1.85 | | 12.28 | 1.54 | 4.55 | | | 0.02 | 314,496.9 |
| 12 | 96.0 | 40 | 0.50 | 0.29 | 0.03 | 0.59 | | 0.22 | 26.02 | 72.25 | | | 0.09 | 18,018.4 |
| 13 | 96.0 | 40 | 9.97 | 73.18 | 1.43 | 1.90 | | 13.01 | 0.05 | 0.44 | | | 0.02 | 431.3 |
| 14 | 96.0 | 40 | 9.97 | 73.18 | 1.43 | 1.90 | | 13.01 | 0.05 | 0.44 | | | 0.02 | 296,047.3 |
| 15 | 3.5 | 40 | 31.88 | 21.78 | 2.33 | 19.16 | | 15.72 | 0.70 | 6.15 | | | 2.29 | 236.7 |
| 16 | 3.5 | 40 | 0.09 | 0.00 | 0.00 | 0.34 | | 0.01 | 26.45 | 73.39 | | | 0.06 | 17,719.7 |
| 17 | | | | | | | | | | | | | | — |
| 41 | 29.0 | 233 | | | | | | | 100.00 | | | | | 22,108.5 |

TABLE 5

| Line number | Pressure Kg/cm$^2$-G | Temp. °C. | Composition (mol %) | | | | | | | | | | | Flow rate kmol/hr |
|---|---|---|---|---|---|---|---|---|---|---|---|---|---|---|
| | | | CH$_4$ | H$_2$ | CO | CO$_2$ | O$_2$ | N$_2$ | H$_2$O | CH$_3$OH | C$_2$H$_6$ | C$_3$H$_8$ | Others | |
| 1 | 27.0 | 40 | 95.60 | | | 0.47 | | 0.26 | 0.01 | | 3.39 | 0.09 | 0.18 | 13,236.3 |
| 2 | 25.0 | 560 | 26.62 | | | 0.13 | | 0.07 | 72.16 | | 0.94 | 0.03 | 0.05 | 47,537.0 |
| 3 | | | | | | | | | | | | | | — |
| 4 | 19.4 | 777 | 6.23 | 47.60 | 8.93 | 5.52 | | 0.05 | 31.68 | | | | | 66,673.1 |
| 5 | | | | | | | | | | | | | | — |
| 6 | 20.0 | 150 | | | | | 99.00 | 1.00 | | | | | | 2,984.4 |
| 7 | 19.0 | 975 | 0.41 | 50.18 | 13.23 | 4.89 | | 0.09 | 31.32 | | | | | 74,399.3 |
| 9 | 17.0 | 40 | 0.59 | 72.64 | 19.15 | 7.08 | | 0.13 | 0.41 | | | | | 51,389.8 |
| 10 | 100.0 | 240 | 2.67 | 87.87 | 5.41 | 3.00 | | 0.60 | 0.12 | 0.30 | | | 0.02 | 229,493.1 |
| 11 | 98.0 | 260 | 3.02 | 84.65 | 1.33 | 1.81 | | 0.68 | 1.81 | 6.76 | | | 0.02 | 203,305.1 |
| 12 | 96.0 | 40 | 0.19 | 0.40 | 0.04 | 0.62 | | 0.06 | 21.45 | 77.18 | | | 0.10 | 16,859.9 |

TABLE 5-continued

| Line number | Pressure Kg/cm$^2$-G | Temp. °C. | Composition (mol %) | | | | | | | | | | Flow rate kmol/hr |
| --- | --- | --- | --- | --- | --- | --- | --- | --- | --- | --- | --- | --- | --- |
| | | | CH$_4$ | H$_2$ | CO | CO$_2$ | O$_2$ | N$_2$ | H$_2$O | CH$_3$OH | C$_2$H$_6$ | C$_3$H$_8$ | Others | |
| 13 | 96.0 | 40 | 3.27 | 92.26 | 1.45 | 1.83 | | 0.39 | 0.74 | 0.39 | | | 0.02 | 8,342.0 |
| 14 | 96.0 | 40 | 3.27 | 92.26 | 1.45 | 1.83 | | 0.39 | 0.74 | 0.39 | | | 0.02 | 168,859.9 |
| 15 | 3.5 | 40 | 23.26 | 45.68 | 3.72 | 22.63 | | 1.42 | 0.83 | 6.34 | | | 3.66 | 145.7 |
| 16 | 3.5 | 40 | 0.05 | 0.01 | 0.00 | 0.43 | | 0.00 | 21.64 | 77.80 | | | 0.07 | 16,714.2 |
| 17 | 3.5 | 400 | 95.60 | | | 0.47 | | 0.26 | 0.01 | | 3.39 | 0.09 | 0.18 | 3,608.9 |
| 41 | 29.0 | 233 | | | | | | | 100.00 | | | | | 25,081.8 |

The energy efficiency of the whole plant was as shown in Table 6, and the overall unit energy consumption (Gcal/ton-methanol) was 6.809. In this case, however, the amount of heat recovered from the process exceeds significantly the total power requirements of rotary machines, so that if the excess energy is not sold to the outside, it cannot contribute to the accomplishment of the unit energy consumption described above.

heat-exchange type reformer. However, a start-up heater is necessary to start-up the heat-exchange type reformer so that further plant investment is required together with the cost-up of the oxygen related apparatus needed in excess. Accordingly, the above-described conditions of the relation (R)=to be close to 2.0 are not economical from the viewpoints of energy efficiency and investment cost.

TABLE 6

| | Example 1 | Example 2 | Example 3 | Comp. Ex.1 | Comp. Ex. 2 |
| --- | --- | --- | --- | --- | --- |
| Relation (R) among mol % of H$_2$, CO and CO$_2$ in synthesis gas | 2.5 | 2.5 | 2.25 | 2.0 | 2.5 |
| Consumption of feedstock natural gas (Gcal/t-methanol) ① | 6.306 | 6.255 | 6.132 | 6.132 | 6.255 |
| Fuel requirements of fired-heating type reformer (Gcal/hr) | 321.04 | 653.64 | 334.01 | 43.92 | 1,223.21 |
| Amount of purge gas for fuel (Gcal/hr) | −517.53 | 520.44 | −275.26 | −47.99 | −520.44 |
| Net consumption of fuel natural gas (Gcal/hr) | 106.30 | 133.20 | 58.75 | −4.07 | 702.77 |
| Net consumption of fuel natural gas (Gcal/t-methanol) ② | 0.227 | 0.320 | 0.141 | −0.010 | 1.687 |
| Oxygen requirements (Nm$^3$/hr) | 73,186 | 66,222 | 102,716 | 138.806 | 66,222 |
| Amount of synthesis make-up gas (Nm$^3$/hr) | 1,151,396 | 1,151,851 | 1,072,005 | 999,125 | 1,151,851 |
| Power requirements of air compressor (kW) A | 18,500 | 16,740 | 25,965 | 35,087 | 16,740 |
| Power requirements of oxygen compressor (kW) B | 10,355 | 9,370 | 14,533 | 19,639 | 9,370 |
| Power requirements of synthesis gas/circulating gas compressor (kW) C | 53,599 | 53,639 | 50,674 | 49,146 | 53,639 |
| Total power requirements (kW) A + B + C | 82,454 | 79,749 | 91,171 | 103,873 | 79,749 |
| Energy consumption corresponding to power requirements (Gcal/t-methanol) ③ | 0.567 | 0.549 | 0.627 | 0.715 | 0.549 |
| Process heat recovery (Gcal/t-methanol) ④ | −0.408 | −0.410 | −0.189 | 0.011 | −1.682 |
| Overall unit energy consumption (Gcal/t-methanol) ① + ② + ③ + ④ | 6.692 | 6.714 | 6.711 | 6.848 | 6.809 |

As illustrated in Table 6, it has become clear that it does not necessarily optimize the overall energy efficiency of the methanol plant to produce a synthesis gas having a molar relation among CO$_2$, CO and H$_2$ called the stoichiometric ratio (R=2) in the methanol synthesis. Namely, as the relation (R) becomes smaller, the amount of oxygen required is increased and the power requirements of the air compressor to supply air to the air separation unit and the power requirements of the oxygen compressor are also increased correspondingly.

In other words, as the relation (R) is closer to the stoichiometric ratio, power requirements of the compressor for the synthesis make-up gas is reduced. However, the total power consumption, together with the power requirements of the air compressor and the oxygen compressor, is increased offsetting the above-mentioned power reduction.

As a result, it has become apparent that the overall energy efficiency including process heat recovery turns contrariwise worse by further cancelling even the reduction in the requirements of feedstock and fuel natural gas. The turning point is found to be at a value of the relation (R) to be around 2.25.

When the relation (R) is made close to 2.0, the primary steam reforming can be effected substantially only by the In accordance with the cost of natural gas and in consideration of the economical efficiency taking into account primarily apparatus of large equipment costs, including the combustion type steam reforming furnace, air separator and large rotary machines, it has been found that the relation (R) among the mol percentages of CO$_2$, CO and H$_2$ in the synthesis gas should be selected and designed in the range of 2.2–2.5.

As has been described above, according to the present invention, the energy efficiency of a whole process for the production of methanol including the production of synthesis gas is improved in comparison with the conventional processes and the construction cost of the process plant is also reduced.

What is claimed is:

1. A process for producing methanol which comprises subjecting a feedstock gas comprising hydrocarbons having atomic ratios H/C of hydrogen (H) to carbon (C) of 3–4 or a feedstock gas formed by treating hydrocarbons having atomic ratios H/C of 2–3 in a prereformer to primary reforming under the conditions of a pressure of 15–40 Kg/cm$^2$-G, a catalyst outlet temperature of 750–850° C. and a molar ratio S/C of steam (S) to carbon (C) in the feedstock gas of 2.5–4.0 and then to secondary reforming using oxygen having a purity of 95% or more under the conditions of a pressure of 15–40 Kg/cm$^2$-G and a catalyst outlet temperature of 950–1,000° C. to obtain a synthesis gas in which the relation (R) among the mol percentages of hydrogen, carbon monoxide and carbon dioxide is 2.2–2.5 as calculated according to the following equation $$R=(H_2 \text{ mol \%} - CO_2 \text{ mol \%})/(CO \text{ mol \%} + CO_2 \text{ mol \%})$$

and subjecting said synthesis gas to methanol synthesis at a pressure of 40–100 Kg/cm$^2$-G and a catalyst temperature of 210–300° C. to produce methanol, wherein said primary reforming comprises a fired-heating steam reformer and heat-exchange steam reformer, said feedstock gas with sulfur removed is mixed with steam to obtain a feedstock mixed gas having an S/C of 2.5–4.0, the feedstock mixed gas is fed to said fired-heating steam reformer and said heat exchange steam reformer in a proportion to said fired-heating steam reformer and to said heat exchange steam reformer of 1 to 3–3 to 1, said fired-heating steam reformer is effected by using as the heat source a combustion gas formed by burning part of said feedstock gas with sulfur removed and a synthesis purge gas generated to remove inert components accumulated in the methanol synthesis loop, the combustion gas discharged from said fired-heating steam reformer is heat-exchanged with said feedstock mixed gas introduced into said fired-heating steam reformer to heat said feedstock mixed gas, while said heat-exchange steam reformer is effected by causing said feedstock mixed gas to exchange heat with said synthesis gas from said secondary reformer to heat said feedstock mixed gas, and steam generated by the recovery of the reaction heat in said methanol synthesis is used as steam for mixing with said feedstock gas supplied to said primary reforming.

2. The process according to claim 1 wherein said combustion gas is obtained by burning a synthesis gas which has been dissolved in methanol discharged from the methanol synthesis and is evolved by reducing the pressure of the methanol to atmospheric pressure, in addition to the part of the feedstock gas and the synthesis purge gas.

3. The process according to claim 1, wherein an effluent gas comprising methanol and unreacted synthesis gas, the heat content of which was recovered by generating steam and which was discharged from the methanol synthesis, is heat-exchanged with the synthesis gas to be introduced into the methanol synthesis to heat said synthesis gas.

4. The process according to claim 1, wherein the synthesis gas discharged from said secondary reformer and heat-exchanged in said heat-exchange steam reformer is cooled by exchanging heat with water for generating steam used for the heat recovery in the methanol synthesis.

* * * * *